United States Patent [19]

Scott et al.

[11] Patent Number: 4,523,038

[45] Date of Patent: Jun. 11, 1985

[54] ALDEHYDE ADDUCTS AND A PROCESS FOR SEPARATING ALDEHYDES INVOLVING THEM

[75] Inventors: Norman Scott, Stockton-On-Tees; Paul Hepworth, Upper Poppleton, both of England

[73] Assignee: Imperial Chemical Industries PLC, England

[21] Appl. No.: 606,943

[22] Filed: May 4, 1984

Related U.S. Application Data

[60] Division of Ser. No. 482,986, Apr. 7, 1983, Pat. No. 4,480,139, which is a continuation of Ser. No. 282,953, Jul. 13, 1981, abandoned.

[30] Foreign Application Priority Data

Jul. 22, 1980 [GB] United Kingdom ............... 8023888

[51] Int. Cl.$^3$ ............................................ C07C 45/78
[52] U.S. Cl. .................................................. 568/492
[58] Field of Search ................................. 568/492, 486

[56] References Cited

U.S. PATENT DOCUMENTS

| | | | |
|---|---|---|---|
| 2,673,222 | 3/1954 | McAteer et al. | 568/923 |
| 3,492,356 | 1/1970 | Hall | 568/492 |
| 3,790,640 | 2/1974 | Kurosaki et al. | 568/680 |
| 3,897,503 | 7/1975 | Wessendorf et al. | 568/486 |
| 3,931,338 | 1/1976 | Rupilius et al. | 568/680 |
| 4,006,189 | 2/1977 | Sommer et al. | 568/492 |
| 4,448,977 | 5/1984 | Warner et al. | 568/486 |

FOREIGN PATENT DOCUMENTS

| | | | |
|---|---|---|---|
| 0044650 | 1/1982 | European Pat. Off. | 568/492 |
| 2139211 | 2/1973 | Fed. Rep. of Germany | 568/492 |
| 2329957 | 1/1975 | Fed. Rep. of Germany | 568/492 |
| 1454480 | 2/1977 | United Kingdom | 568/492 |
| 168670 | 6/1965 | U.S.S.R. | 568/492 |

OTHER PUBLICATIONS

Barton and Ollis, Comprehensive Organic Chemistry, vol. 1 (1979), p. 962 equation 26.

*Primary Examiner*—Werren B. Lone
*Attorney, Agent, or Firm*—Cushman, Darby & Cushman

[57] ABSTRACT

Linear aldehydes having 7–21 carbon atoms are separated from mixtures (which may contain alcohols and/or branched aldehydes) by converting them into solid adducts with $C_2$ to $C_{12}$ linear alkane diols. The adducts are then separated and decomposed. The adducts are themselves novel compounds.

13 Claims, No Drawings

ALDEHYDE ADDUCTS AND A PROCESS FOR SEPARATING ALDEHYDES INVOLVING THEM

This is a division of application Ser. No. 482,986, filed Apr. 7, 1983 now U.S. Pat. No. 4,480,139 which in turn is a continuation of Ser. No. 282,953 filed July 13, 1981, now abandoned.

This invention relates to aldehyde adducts and a process for separating aldehydes involving them.

It is known to produce long chain aldehydes having for example 7–21 carbon atoms by reacting a corresponding olefine containing one less carbon atom with carbon monoxide and hydrogen. The process may if desired be carried out under conditions such that the aldehyde which is first formed is further converted into alcohol. Processes of this type may produce a certain amount of α-branched chain product and/or alcohol even if the starting olefine is linear.

For certain purposes a linear aldehyde free from branched material and/or alcohol may be required, but it may be difficult to effect such separations by conventional means; for example the separation of branched from linear materials by distillation may be difficult.

The invention comprises a process of separating a linear aldehyde having 7–21 preferably 11–17 and more preferably 13–16 carbon atoms from a mixture comprising it, for example a mixture which also comprises an alcohol or a branched aldehyde especially one containing an α-alkyl group, which comprises converting the linear (normal) aldehyde to a solid adduct with an α,ω-linear alkane diol having 2–12 and preferably 2–6 carbon atoms by contacting it with the said diol, separating the solid adduct and decomposing the adduct to regenerate the linear aldehyde and the diol.

It is preferred that the diol should be butane 1,4 diol, though ethylene glycol may also be preferred because of its cheapness and ready availability. Even carbon numbered diols are preferred to odd numbered ones.

The adduct is believed to have the formula

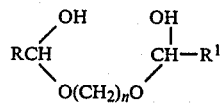

where R and R¹ are individually alkyl groups having 6 to 20 preferably 10 to 16 and more preferably 12 to 15 carbon atoms and n is an integer in the range 2 to 12 and preferably 2 to 6. These compounds are believed to be novel, and their ease of decomposition makes them especially suitable for the process of the invention.

Suitably an excess of the diol in the range 1 to 5 moles and preferably 1 to 2 moles per mole of linear (normal) aldehyde is present during the formation of the adduct.

When a high proportion of crystals are formed the product may solidify. For ease of handling it may therefore be preferred to form the crystals of the adduct in the presence of an inert solvent, for example petroleum ether or preferably a $C_3$ to $C_8$ ketone especially acetone. It has also been found that the size of crystals of the solid adduct is increased by forming them in the presence of nucleation inhibitor for example triphenyl phosphine.

The formation of the adduct is preferably carried out at a temperature in the range 10° to 30° C. When formed it may if desired be washed for example with the corresponding linear aldehyde or with any other suitable liquid for example petroleum ether or a lower ketone, for example a ketone having 3 to 8 carbon atoms for example acetone.

The adduct may be decomposed by heating for example to a temperature above 30° C. which is suitably in the range 30° to 100° C., and more preferably 30° to 80° C. or by treating it with water, an acid, for example p-toluene sulphonic acid, or a base for example sodium or potassium carbonate suitably at a temperature of 30° to 100° C. and more preferably 30° to 80° C.

The process according to the invention may be carried out as a cyclic process in which the aldehyde mixture is mixed with agitation with the diol to produce the solid adduct, the solid adduct is separated by filtration and optionally washed with the pure linear aldehyde, the wash liquid is returned to the starting aldehyde mixture, and the remaining solid is decomposed by heating to regenerate purifed linear aldehyde and the diol. Filtrates containing branched aldehyde and ethylene glycol usually settle into an ethylene glycol rich layer and a branched aldehyde rich layer. The ethylene glycol rich layer may be returned to the first stage of the process.

In general, some linear aldehydes remain in the liquid. It is possible to reduce the quantities so remaining by carrying out the process at a lower temperature. If the mixture contains very little linear aldehyde, usually no adduct is precipitated.

It appears that when more than one linear aldehyde is present, the higher aldehyde precipitates preferentially. Thus, the adduct which is recovered tends to be richer in the higher homologue than the starting mixture, and this is particularly marked if the amount of adduct produced is considerably less than the maximum amount which could be produced. Thus, by taking successive yields of adduct from a mixture by successive treatments with the diol the ratios of the homologues in each successive yield will change, the higher homologue being present in the greatest amount in the first yield and the lowest in the last.

If it is desired to separate a linear aldehyde from a mixture from which, because of its lower concentration, its adduct will not precipitate, precipitation may be induced by adding a suitable lower linear aldehyde. Such an aldehyde should be selected for its effectiveness in inducing the precipitation and, if it is desired to recover it, for its easy separability from the mixture. The lower linear aldehyde may be supplied in admixture with corresponding branched aldehydes providing that its concentration in the mixture is sufficiently high for it to be effective.

Higher diols tend to react preferentially compared with lower diols, and if desired the viscosity of the mixture may be reduced by forming an adduct of a higher diol in the presence of a lower diol (for example ethylene glycol) as a viscosity reducer.

EXAMPLE 1

Mixed $C_{13}/C_{15}$ aldehydes (100 g) were mixed with ethylene glycol (16 g) between 25° to 30° C. for 24 hours. The mixture was gently agitated and after 3 hours had become a very thick paste. At the end of the reaction the solid was filtered off and washed well with acetone to remove any unreacted aldehyde and dried at room temperature. This yielded 22.3 g of a solid ethylene glycol/linear aldehyde adduct M.Pt. 47° C. GLC analysis showed that the starting aldehyde mixture consisted of:

| Branched $C_{13}$ % w/w | Linear $C_{13}$ % w/w | Branched $C_{15}$ % w/w | Linear $C_{15}$ % w/w |
| --- | --- | --- | --- |
| 35.6 | 32.8 | 18.1 | 13.5 |
| Recovered aldehydes had the following analysis | | | |
| 46.7 | 23.9 | 23.3 | 6.1 |
| The adduct when decomposed (by for example dissolving it in chloroform) gave adehydes of the following analysis. | | | |
| 0.8 | 59.4 | not detectable | 39.8 |

Calculation showed:
1. 41.8% Linear $C_{13}$ aldehyde was converted to adduct.
2. 68.1% Linear $C_{15}$ aldehyde was converted to adduct.
3. 49.9% of the available linear aldehydes were converted to adduct.

Infra red analysis of the adduct showed it to be a compound formed between ethylene glycol and aldehyde which slowly reverted to glycol and aldehydes at elevated temperatures.

N.M.R. analysis in chloroform gave a spectrum for 2 moles linear aldehyde mixed with 1 mole ethylene glycol.

EXAMPLE 2

Mixed $C_{13}/C_{15}$ aldehydes (100 g) with a similar analysis to those of example 1 were mixed with 1,4-butane diol (25 g), between 25° and 30° C. for 24 hours. The mixture was gently agitated but after 6 hours had become a thick paste. At the end of the reaction the solid was filtered, washed well with acetone to remove any unreacted aldehydes and dried at room temperature. This yielded 38.6 g of a solid 1.4 butane diol/linear aldehyde adduct M.Pt. 50° C. G.L.C. analysis showed that the recovered unreacted aldehyde (58.7 g) had the following analysis.

| Branched $C_{13}$ | Linear $C_{13}$ | Branched $C_{15}$ | Linear $C_{15}$ |
| --- | --- | --- | --- |
| 55.2 | 13.2 | 28.6 | 3.0 |
| The adduct when decomposed (by for example dissolving it in petroleum ether (80–100° C.) gave aldehydes of the following analysis. | | | |
| 0.1 | 66.9 | — | 33.0 |

Calculation showed:
1. 73.6% of the linear $C_{13}$ aldehyde was converted to adduct.
2. 88.2% of the linear $C_{15}$ aldehyde was converted to adduct.
3. 78% of the available linear aldehydes were converted to adduct.

Infra red analysis of the adduct showed it to be a compound formed between 1,4 butane diol and linear aldehyde with long carbon chain crystallinity.

The NMR spectrum in chloroform showed it to have 2 moles linear aldehydes with 1 mole butane diol.

Examination of crystals of the adduct by nuclear magnetic resonnance gave chemical shifts of carbon 13 as compared with tetramethyl silane as a standard of

| | |
| --- | --- |
| 15.27 ppm | 39.54 ppm |
| 25.05 ppm | 68.20 ppm |
| 28.42 ppm | 98.60 ppm |
| 33.14 ppm | |

This indicates that the adduct is a hemiacetal of structure $$RCH\begin{matrix}OH\\ \\O(CH_2)_4O\end{matrix}\begin{matrix}HO\\ \\ \end{matrix}CH-R^1$$

where R and $R^1$ are alkyl groups derived from the aldehyde.

EXAMPLE 3

Mixed $C_{13}/C_{15}$ aldehydes (100 g) of similar composition to Example 1 were mixed with 1,8-octane diol (40 g). The mixture was warmed to 70° C. to melt the diol and cooled to room temperature. The mixture slowly solidified and after 1 hour was suspended in acetone, washed with acetone and dried at room temperature. This yielded 44.8 g of a solid 1,8 octane diol adduct with linear aldehyde. M.Pt. 56° C.

GLC analysis showed the recovered unreacted aldehyde (66.8 g) to have the following analysis.

| Branched $C_{13}$ % w/w | Linear $C_{13}$ % w/w | Branched $C_{15}$ % w/w | Linear $C_{15}$ % w/w |
| --- | --- | --- | --- |
| 52.4 | 16.1 | 27.5 | 4.0 |
| The adduct when decomposed in chloroform solution gave the following aldehyde analysis. | | | |
| 0.3 | 66.7 | — | 33.0 |

Calculation showed:
1. 67.5% of the linear $C_{13}$ aldehyde was converted to adduct.
2. 79.4% of the linear $C_{15}$ aldehyde was converted to adduct.
3. 71.1% of the available linear aldehydes were converted to adduct.

Infra red analysis of the adduct showed it to be a compound of 1,8-octane diol and aldehyde in the same family as those formed by aldehyde with 1,4-butane diol or ethylene glycol. This spectrum also showed long carbon chain crystallinity.

EXAMPLE 4

Mixed $C_{13}/C_{15}/C_{17}$ aldehydes (100 g) were mixed with 1,6-hexanediol (30 g), warmed to 60° C. to melt the diol and allowed to cool to room temperature and left for 18 hours before working up as in Example 1 with acetone. The starting aldehyde mixture contained the following linear aldehydes

| Linear $C_{13}$ % w/w | Linear $C_{15}$ % w/w | Linear $C_{17}$ % w/w |
| --- | --- | --- |
| 1.0 | 19.3 | 5.3 |

The adduct (MPt 56° C.) shown by infra red spectroscopy to be in the same family as those obtained with examples 1–3, had the following aldehyde analysis by GLC.

| Linear C$_{13}$ | Linear C$_{15}$ | Linear C$_{17}$ |
| --- | --- | --- |
| 2.1 | 75.5 | 22.3 |

EXAMPLE 5

Dodecanal (5 g) was reacted with 1,4-butane diol (1 g) by warming the mixture to 50° C. in order to melt the dodecanal and then allowing it to cool to room temperature. The mixture went completely solid and was worked up as in Example 3 with acetone to yield the 1,4-butane diol/dodecanal adduct (1.1 g) M.Pt 51° C.

Infra red spectra showed the adduct to be in the same family as Examples 1 to 4 and it was decomposed readily by chloroform yielding aldehyde and diol.

EXAMPLE 6

1.4-Butane Diol with Octanal

Example 1 was repeated using 1,4-butane diol with octanal, except the reaction mixture was cooled to 5° C. when a crystalline precipitate was obtained M.Pt. 34° C.

Infra red analysis showed this to be in the same family as products in Examples 1 to 5.

EXAMPLE 7

Regeneration of C$_{13}$/C$_{15}$ aldehyde from its adduct with 1,4-butane diol produced in Example 2

Adducts (19.92 g) and water (20 g) was placed in a separating funnel and warmed to 60° C. The adduct melted at about 50°-55° C. and two layers were obtained. The bottom water layer was shown by gas/liquid chromatography to contain 1,4-butane diol. This was separated and the upper layer washed a further twice with 20 g water.

The aldehyde regenerated was shown to be 99.9% linear. Yield of aldehyde, 16.2 g which represented a 99% recovery from the adduct.

EXAMPLE 8

Regeneration of the adduct of Example 1 was carried out by the procedure of Example 7 except that 15 g of adduct were used. This gave 12.8 g of the C$_{13}$/C$_{15}$ aldehyde mixture which was 99.9% linear and recovery was essentially 100% from the adduct.

EXAMPLE 9

Preparation of C$_{13}$/C$_{15}$ aldehyde adduct in the presence of 1,4-butane diol and ethylene glycol The presence of mixed glycols reduces the viscosity build up of the reaction mixture.

Mixed C$_{13}$/C$_{15}$ aldehydes (100 g) with a similar analysis to Example 1 were mixed with ethylene glycol (8 g) and 1,4-butane diol (12 g) and allowed to react for 24 hours at 25°-30° C. The mixture remained much more mobile than in either Example 1 or 2. At the end of the reaction the product was worked up as in Example 1. This yielded 36.2 g of adduct (MPt 51° C.) which was shown by infra red spectroscopy to be identical with the 1,4-butane diol adduct in Example 2. Ethylene glycol had not taken part in the reaction. This was further proved by decomposing adduct as in Example 8 when no trace of ethylene glycol was found in the water layer. Calculation showed 1. 62.1% of the linear C$_{13}$ aldehyde was converted to adduct.
2. 80.7% of the linear C$_{15}$ aldehyde was converted to adduct.
3. 71.7% of the available linear aldehydes were converted to adduct.

Regeneration of the aldehyde by the method of Example 8 gave 99.9% pure linear aldehydes with a 99.5% yield of aldehyde from the adduct.

EXAMPLE 10

Example 2 was repeated except that 7% by weight of acetone was added to the aldehyde mixture before admixture with 1,4-butene diol. The slurry produced was more mobile and more easily filterable than that of Example 2 and the yields and purities were similar.

EXAMPLE 11

Example 2 was repeated except that 0.4% by weight of triphenyl phosphine was added to the aldehyde mixture before admixture with 1,4-butene diol. The crystals produced were larger than those produced in Example 2 by a factor of about 10, leading to much easier filtration and washing. Infra red examination indicated that the crystals after washing with acetone were of high purity and were substantially free from triphenyl phosphine.

EXAMPLE 12

Mixed C$_{13}$/C$_{15}$ aldehydes (70 g) with a similar analysis to those of Example 1 were mixed with acetone (7 g) and triphenyl phosphine (0.45 g) and then treated with 1,4-butane diol (14 g) and left at 25°-30° C. for 24 hours. The mixture was gently agitated but after 3 hours had become a thick paste. At the end of the reaction the solid was filtered, washed well with acetone to remove any unreacted aldehydes and triphenyl phosphine and dried at room temperature. This yielded 35.9 g of a solid 1,4-butane diol/linear aldehyde adduct of melting point 50° C.

The aldehyde regenerated from the adduct as in Example 7 gave a yield of product of similar purity.

NMR means nuclear magnetic resonance spectroscopy. GLC means gas/liquid chromatography. The branched aldehydes of the Examples comprised α-branched aldehydes.

We claim:

1. A process of separating a linear aldehyde having 7 to 21 carbon atoms from a mixture comprising the linear aldehyde, which process comprises the steps of (a) converting the linear aldehyde to a solid adduct with an α, ω linear alkane diol having 2 to 12 carbon atoms by reacting the adehyde with the diol, (b) separating the solid adduct and (c) decomposing the solid adduct to regenerate the linear aldehyde and the diol.

2. A process as claimed in claim 1 in which the mixture comprising the linear aldehyde also comprises a branched aldehyde.

3. A process as claimed in claim 2 in which the branched aldehyde has the same number of carbon atoms as the linear aldehyde.

4. A process as claimed in claim 1 in which the linear aldehyde has 13 to 16 carbon atoms and the α, ω linear alkane diol has 2 to 6 carbon atoms.

5. A process as claimed in claim 1 which is carried out in the presence of an excess of the diol of 1 to 2 moles per mole of linear aldehyde present.

6. A process as claimed in claim 1 wherein step (a) is practiced at a temperature in the range 10° to 30° C. and wherein step (c) is practiced at a temperature in the range 30° to 80° C.

7. A process as claimed in claim 1, wherein step (a) is practiced by forming the solid adduct in the presence of an inert solvent for the aldehyde.

8. A process as claimed in claim 1, wherein step (a) is practiced by forming the solid adduct in the presence of a nucleation inhibitor.

9. A process as claimed in claim 1 in which the mixture further comprises higher and lower linear aldehydes, the higher linear aldehyde being separated preferentially from the mixture by forming an amount of solid adduct substantially less than the maximum amount which could be formed.

10. A process of separating a linear aldehyde having 7 to 21 carbon atoms from a mixture comprising the linear aldehyde, the process comprising the steps of converting the linear aldehyde to a solid adduct with an α,ω linear alkane diol having 2 to 12 carbon atoms, which solid adduct is of the formula

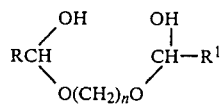

where R and $R^1$ are individually alkyl groups having 6 to 20 carbon atoms and n is an integer in the range 2 to 12 by reacting the said aldehyde with the said diol, separating the solid adduct and decomposing the solid adduct to regenerate the linear aldehyde and the diol.

11. A process as in claim 10 wherein the mixture further comprises a branched aldehyde.

12. A process as in claim 11 wherein the branched aldehyde has the same number of carbon atoms as the linear aldehyde.

13. A process as in claim 11 wherein the mixture further comprises higher and lower linear aldehydes the higher linear aldehyde being separated preferentially from the mixture by forming an amount of solid adduct substantially less than the maximum amount which could be formed.

* * * * *